United States Patent [19]
Freedman et al.

[11] Patent Number: 5,443,802
[45] Date of Patent: Aug. 22, 1995

[54] STERILIZATION OF FERMENTATION EQUIPMENT WITH SHROUD ASSEMBLY

[75] Inventors: David Freedman; Yinliang Chen, both of Highland Park; Zhenbin Zheng, Edison, all of N.J.

[73] Assignee: New Brunswick Scientific Co., Inc., Edison, N.J.

[21] Appl. No.: 99,622

[22] Filed: Jul. 29, 1993

[51] Int. Cl.6 .............................................. A61L 2/20
[52] U.S. Cl. ..................... 422/298; 422/26; 422/111; 422/112; 422/202; 422/295; 422/302; 435/311; 435/316
[58] Field of Search ................. 422/26, 307, 108, 110, 422/112, 118, 198, 202, 302, 295, 292, 298; 435/311, 316, 800, 812

[56] References Cited

U.S. PATENT DOCUMENTS

| | | |
|---|---|---|
| 573,289 | 12/1898 | Pridham .......................... 435/311 X |
| 3,209,673 | 10/1965 | Howard ........................... 422/302 X |
| 4,111,654 | 9/1978 | Fahlvik et al. . |
| 4,284,600 | 8/1981 | Gillis et al. . |
| 4,324,762 | 4/1982 | Redikultsev et al. . |
| 4,552,720 | 11/1985 | Baker, Sr. et al. . |
| 4,746,615 | 5/1988 | Buchholz et al. ................... 435/311 |
| 4,748,003 | 5/1988 | Riley . |
| 4,781,898 | 11/1988 | Jones . |
| 5,026,524 | 6/1991 | Powell et al. . |

Primary Examiner—Amalia L. Santiago
Attorney, Agent, or Firm—Richard C. Woodbridge

[57] ABSTRACT

The present invention relates to in-place sterilization of a fermentation vessel assembly and media. Media can be contained in reagent bottles placed on the fermentation vessel assembly or can be contained in a fermentation vessel which is part of the fermentation vessel assembly. A removable shroud covers the fermentation vessel assembly and media during sterilization. Steam is applied inside the shroud for raising the temperature within the shroud to a sterilization temperature.

11 Claims, 3 Drawing Sheets

STERILIZATION OF FERMENTATION EQUIPMENT WITH SHROUD ASSEMBLY

BACKGROUND OF THE INVENTION

1. Field of the Invention

This invention relates to a method and apparatus for in-place sterilization of fermentation equipment including liquid media.

2. Description of the Related Art

It is known that an autoclave can be used to sterilize articles used in fermentation, such as a fermentor vessel. U.S. Pat. No. 4,111,654 describes an autoclave apparatus including a chamber in which articles are steam sterilized. The chamber is surrounded by an outer space having a steam supply conduit. A constant pressure difference between the chamber and the outer space permits thermodynamically optimum steam flow to the chamber with minimal energy loss. However, the use of an autoclave for sterilization has the shortcoming that the articles must be removed from the fermentor, transported to the autoclave and placed inside the autoclave.

U.S. Pat. No. 5,026,524 describes an apparatus to subject culture media and instruments to temperatures below 100° C., as defined as low temperature sterilization. A sterilization chamber is provided for placement of articles therein. A jacket chamber surrounds the sterilization chamber and is operated to subatmospheric pressure. Steam is introduced into the jacket chamber for providing a preselected temperature within the sterilization chamber. This patent does not disclose in-place sterilization of fermentation equipment.

U.S. Pat. No. 4,324,762 describes an apparatus for sterilization of liquid media used for growing microorganisms in a fermentor. A sterilization vessel includes a heater, heat exchanger, inlet and outlet pipes. A buffer vessel communicates with the sterilization vessel. Initial liquid media is contained in the sterilization vessel and is heated to a sterilization temperature with the heat exchanger. The sterile medium flows from the sterilization vessel to the buffer vessel and is intermittently or continuously supplied to the fermentor. This patent provides in-place sterilization of the medium but does not provide in-place sterilization of the fermentation equipment.

Conventional bench fermentors have provided in-place sterilization of fermentor vessels with external steam or internally produced steam. Typically, the fermentor vessel is formed of high temperature resistant glass or stainless steel with glass windows. Fermentor vessels formed of stainless steel with glass windows have the disadvantage of limited visibility of the fermentation process taking place within the vessel. During the sterilization, a research fermentor with a glass cylinder is still one of the preferred designs. During the sterilization, steam is introduced inside the glass fermentor vessel from an input port. As a result of the introduction of steam or heat, pressure inside the fermentor vessel is greater than atmospheric pressure outside the vessel. This fermentor has the disadvantage that if the glass of the fermentor vessel is weak due to a scratch, blemish or the like, the increased pressure within the vessel can cause the glass of the vessel to break crack or become displaced.

It is desirable to provide an improved assembly for in-place sterilization of fermentation equipment and liquid media.

SUMMARY OF THE INVENTION

Briefly described, the invention comprises a removable shroud for in-place sterilization of fermentation vessel assembly and liquid media. During sterilization, the shroud is placed over the fermentation vessel assembly. Preferably, the shroud entirely covers the head and glass portion of the vessel assembly. Steam is applied inside the shroud at a predetermined temperature and length of time for sterilizing the fermentation vessel assembly. After sterilization, the shroud is removed from the fermentation vessel assembly, thus providing visibility for the fermentation process.

Reagent bottles including acid, base, anti-foam media or reagents can be placed on the top of the head plate and covered by the shroud. The bottles can be connected to the operating section of the fermentation vessel apparatus with tubing. Media can also be contained within the fermentation vessel during sterilization. Accordingly, the present invention provides for in-place balanced sterilization of the glass vessel, and lower vessel assembly as well as the total vessel assembly including addition bottles, tubing and connectors at the same time. The invention will be further understood with reference to the following drawings.

DETAILED DESCRIPTION OF THE INVENTION

During the course of this description like numbers will be used to identify like elements according to the different figures which illustrate the invention.

Figure 1:
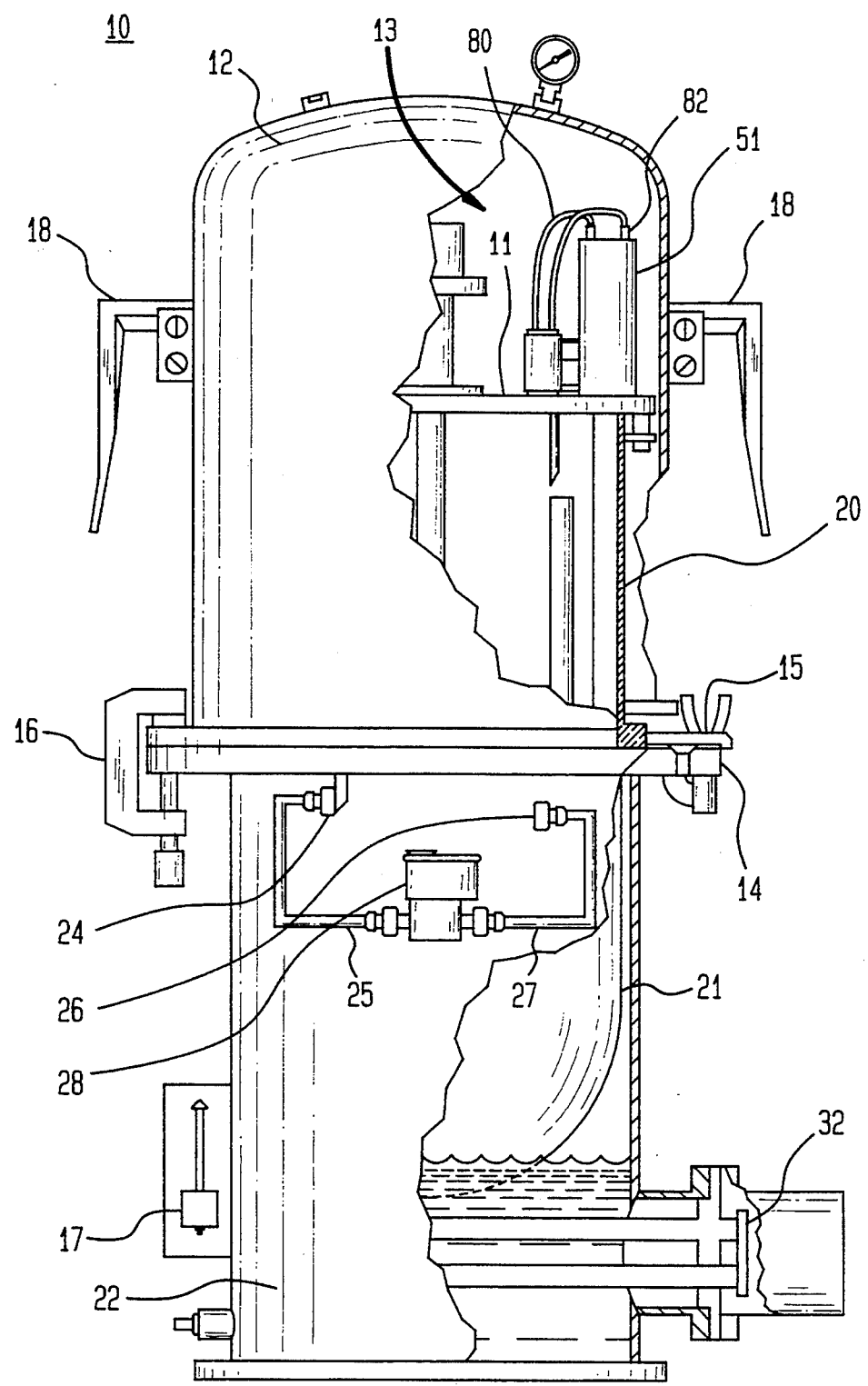
FIG. 1 is a perspective view of the sterilization assembly of the present invention.
Figure 4:
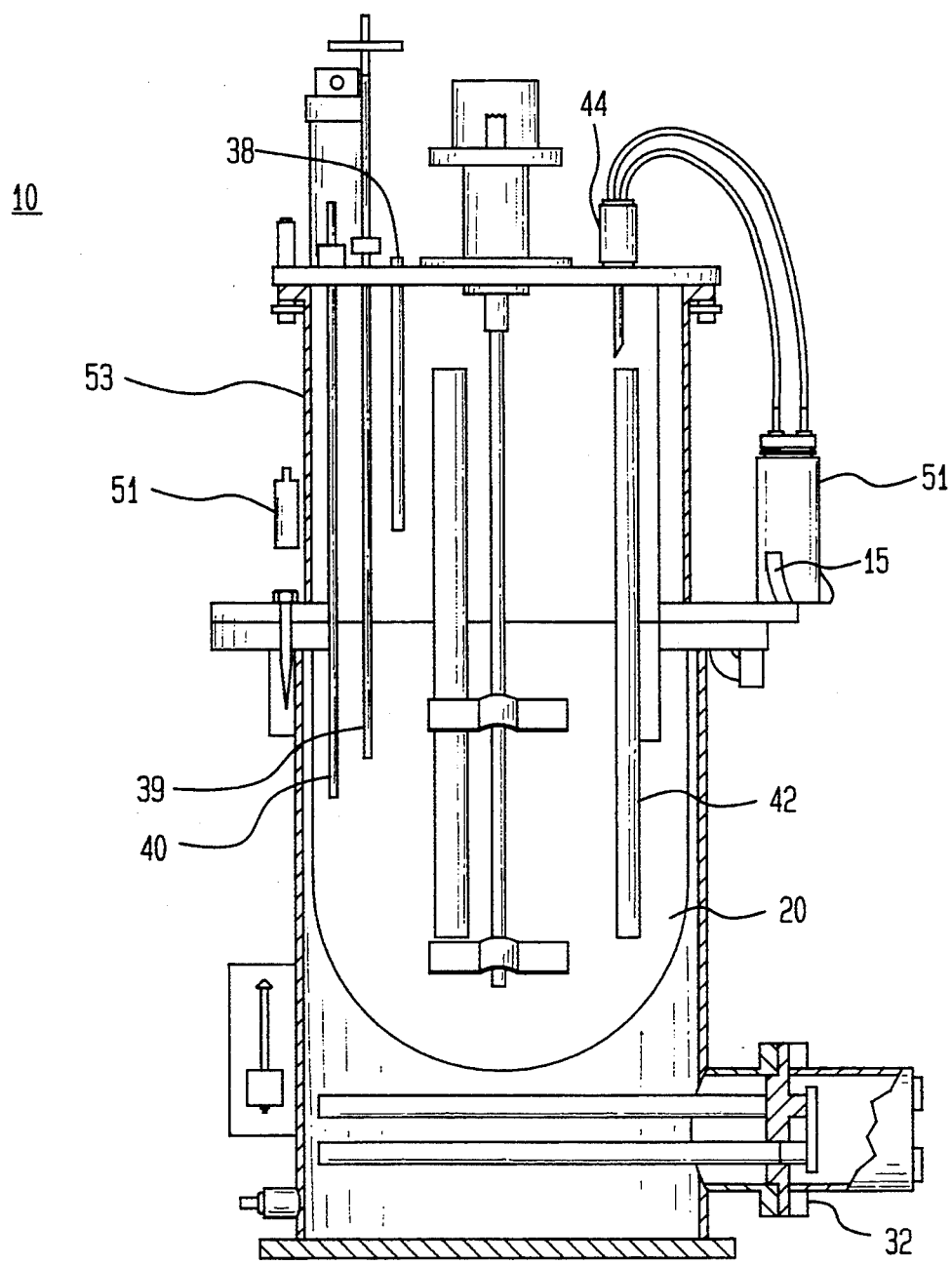
FIG. 4 is a vertical cross-sectional view of the fermentor vessel assembly after sterilization.

FIG. 1 is a perspective view of the sterilization assembly 10 in accordance with the teachings of the present invention. A shroud 12 including an upper flange is placed over fermentation vessel assembly 13. The upper flange of the shroud 12 is mounted to lower vessel flange 14 with clamp 16. Preferably, clamp 16 is a "C-clamp". A ring 15, as shown in FIG. 4, is used when the shroud is removed and placed over lower vessel flange 14 in order to protect the lower flange and its associated O-ring seal from damage.

Shroud 12 is placed over fermentation vessel assembly 13 during sterilization and is unclamped and removed from fermentation vessel assembly 13 after sterilization is complete. Handles 18 can be attached to either side of shroud 12. Shroud 12 can be removed from lower vessel flange 14 by unclamping clamp 16 and lifting up on handles 18.

Fermentation vessel assembly 13 includes vessel 20 anchored to lower vessel flange 14. Vessel 20 can be formed of glass or metal. Preferably vessel 20 is a flanged glass cylinder. Shroud 12 entirely covers vessel 20. A lower portion 21 of vessel 20 is positioned below lower vessel flange 14. Lower portion 21 is supported in base 22. Level switch 17 is used for controlling the water volume within base 22 in order to control temperature in vessel 20 as well as to generate steam for sterilization. An example of vessel assembly 13 used in accordance with the present invention is manufactured by New Brunswick Scientific Co., Inc., as BioFlo III and BioFlo IIC. It will be appreciated that other fermentation equipment could be used with the teachings of the present invention.

Steam is supplied through input port 24 to the inside of shroud 12. Steam can be used to sterilize fermentation vessel assembly 13 before and after each use. Steam input port 24 and stream output port 26 are connected through respective steam connections 25 and 27, which is an outlet of the base 22, to solenoid valve 28. Solenoid valve 28 is opened to allow steam to enter shroud 12 during sterilization and is closed after sterilization to prevent steam or water from entering shroud 12. Heater 32 generates steam as well as heats jacket water 29 in base 22. The pressurized steam passes through solenoid valve 28. Pressure gauge 36 monitors the pressure inside shroud 12 after application of steam from solenoid valve 28. If the monitored pressure/temperature is greater than a predetermined value, solenoid valve 28 can be adjusted in order to control different temperature/pressures inside shroud 12. Preferably, sterilization of fermentation equipment 13 is performed at a pressure between about 17 and 18 psi.

Sterilization of fermentation equipment 13 can be carried out at a standard steam sterilization temperature of about 121° C. or be controlled at other desired temperatures to meet specific applications for a predetermined period. Preferably, steam is supplied to shroud 12 for at least 20 minutes which fulfills most standardized sterilization procedures of fermentation vessel assembly 13. However, duration of sterilization can be adjusted to meet prolonged sterilization requirements.

Figure 2:
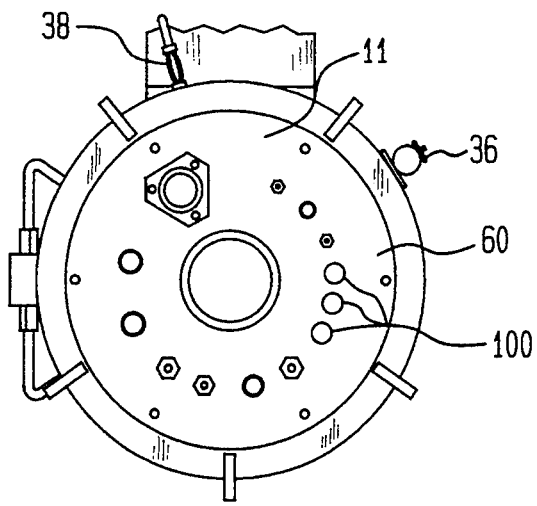
FIG. 2 is a top plan view of fermentation equipment used with the sterilization assembly.

FIG. 2 is a top plan view of fermentation vessel assembly 13 with shroud 12 removed from vessel 20. Head plate 11 attaches to upper portion 53 of vessel 20. In order to control foam and liquid levels, pH, and DO., pumps can be used to deliver materials such as acid, base, anti-foam and nutrient addition into openings 100 of head plate 11.

Figure 3:
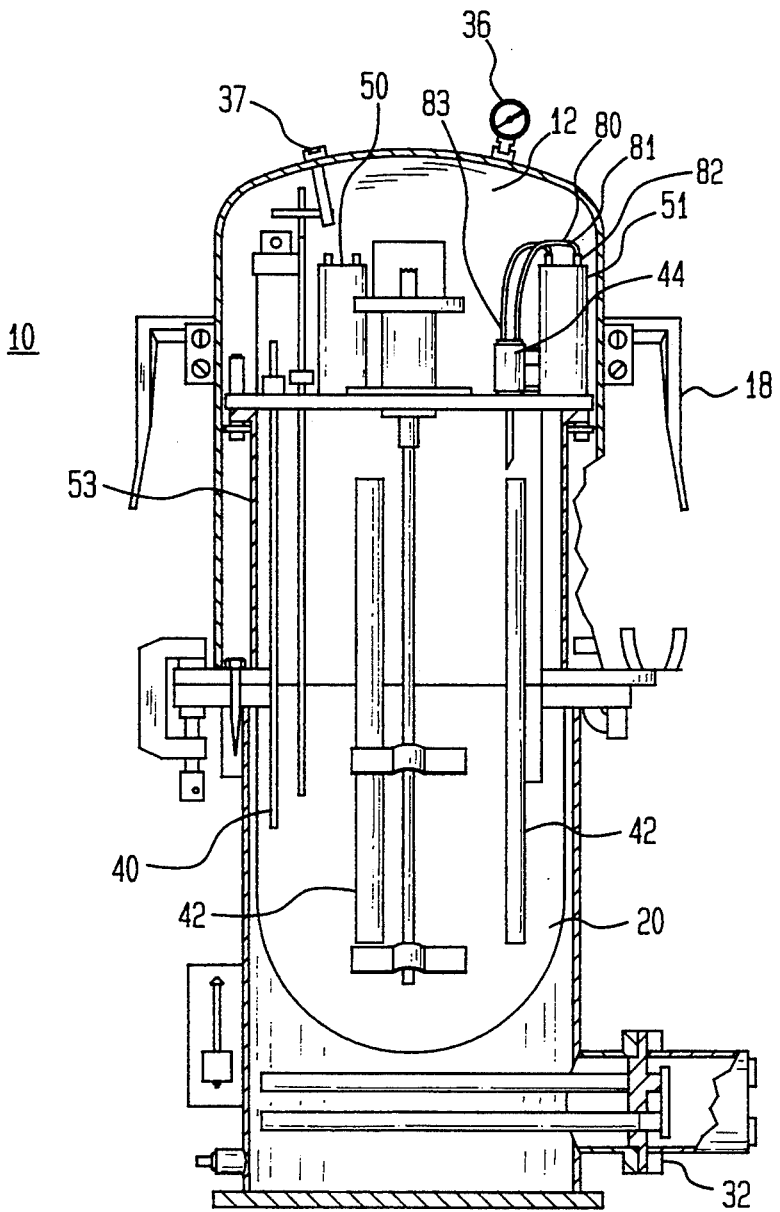
FIG. 3 is a vertical cross-sectional view of the sterilization assembly shown in FIG. 1.

FIG. 3 is a vertical cross-sectional view of sterilization assembly 10. Well port 37 for a temperature probe extends through shroud 12. A temperature probe can be inserted into well port 37 and is used to monitor and control the temperature inside shroud 12 during sterilization. Solenoid valve 28 can be opened or closed in response to received input from temperature probe 38. A dissolved oxygen probe 40 extends into vessel 20. Measurements from temperature probe 38, dissolved oxygen probe 40 and pressure gauge 36 can be forwarded to a personal computer with a fermentation control program, such as is used in the BioFlo III fermentor. The software is also used to control solenoid valve 28.

Media is supplied through input 44 to vessel 20. Reagent bottle 50 is placed on head plate 13 during sterilization. Reagent bottle 50 can contain media or reagents. Reagent bottle 51 can be attached to input 44. End 81 of tubing 80 is connected by connectors 82 to reagent bottle 51. End 83 of tubing 80 is connected to input 44. Baffles 42 can be positioned in vessel 20 for directing flow during fermentation. Application of steam into shroud 12 sterilizes reagent bottles 50, 51 and liquid media or reagents contained therein. It will be appreciated that more than one reagent bottle 50 can be positioned on head plate 11 during sterilization. Application of steam into shroud 12 also sterilizes ports 100 on head plate 11 as well as tubing 80 and connectors 82.

A standard indicator or testing procedure can be used for determining efficiency of steam sterilization. For example, an indicator manufactured by AMSCO Scientific as Proof Plus or "Sterility Tests" of U.S. Pharmacopeia can be used for measuring sterilization of fermentation vessel assembly 13 and media contained in reagent bottles 50, 51 or vessel 20.

FIG. 4 is a vertical cross-sectional view of fermentation vessel assembly 13 after sterilization. Shroud 12 is removed from fermentation vessel assembly 13. Reagent bottle 51 can be repositioned from headplate 11 to ring 15. Well port 38 for a temperature probe extends through headplate 11. A temperature probe can be inserted into well port 38 and is used to monitor and control the temperature of the media in vessel 20.

The present invention has the advantage of providing in-place sterilization of fermentation equipment without producing an increased pressure differential within the reactor vessel. A removable shroud can be easily placed over and clamped on the fermentation vessel assembly during sterilization. The present invention has the additional advantage that media within the fermentation vessel or within reagent bottles placed on the fermentation vessel assembly can be sterilized at the same time as the fermentation equipment is sterilized.

While the invention has been described with reference to the preferred embodiment thereof, it will be appreciated by those of ordinary skill in the art that modifications can be made to the structure and form of the invention without departing from the spirit and scope thereof.

We claim:

1. An apparatus for in-place sterilization of fermentation equipment comprising:
   a base;
   a fermentation vessel attached to said base, said fermentation vessel including a wall;
   steam generation means for producing steam;
   a removable shroud having an interior and selectively attachable to said base for surrounding said fermentation vessel when such shroud is attached to said base; and,
   steam delivery means for selectively delivering steam from said steam generation means to a space defined between said shroud an said fermentation vessel,
   wherein said fermentation vessel can be sterilized in-place.

2. The apparatus of claim 1 wherein said fermentation vessel is substantially transparent.

3. The apparatus of claim 2 wherein said fermentation vessel comprises:
   a glass cylinder having a first and a second end, and wherein said first end is attached to said base.

4. The apparatus of claim 3 further comprising:
   a head plate attached to said second end of said glass cylinder.

5. The apparatus of claim 4 further comprising:
   at least a first container locatable on said head plate; and,
   at least a first connection means for connecting first container to said fermentation vessel,
   wherein said first container and said first connection means are sterilized in-place when said fermentation vessel is sterilized.

6. The apparatus of claim 5 wherein said first container comprises a first reagent bottle containing a first liquid.

7. The apparatus of claim 6 wherein said shroud includes an upper flange and wherein said base includes a lower flange and said apparatus further comprises:
    clamping means for clamping said upper flange of said shroud to said lower flange of said base during sterilization.

8. The apparatus of claim 7 further comprising:
    pressure measuring means for measuring the steam pressure in the interior of said shroud.

9. The apparatus of claim 8 wherein said steam delivery means includes:
    a steam inlet port for supplying steam to the inside of said shroud;
    a solenoid valve attached to said shroud inlet port; and,
    a solenoid valve inlet port for connecting said solenoid valve to said steam generation means,
    wherein said solenoid valve controls the steam pressure on the interior of said shroud.

10. The apparatus of claim 9 wherein said steam generation means is located in said base.

11. The apparatus of claim 10 further comprising:
    temperature measuring means for measuring the temperature in the interior of said shroud.

* * * * *